United States Patent [19]

Barth

[11] Patent Number: 4,536,393

[45] Date of Patent: Aug. 20, 1985

[54] 6-(AMINOMETHYL)PENICILLANIC ACID 1,1-DIOXIDE ESTERS AND INTERMEDIATES THEREFOR

[75] Inventor: Wayne E. Barth, East Lyme, Conn.

[73] Assignee: Pfizer Inc., New York, N.Y.

[21] Appl. No.: 577,478

[22] Filed: Feb. 6, 1984

Related U.S. Application Data

[63] Continuation-in-part of Ser. No. 501,451, Jun. 6, 1983, abandoned.

[51] Int. Cl.$^3$ .................. C07D 499/00; A61K 31/425
[52] U.S. Cl. ............................ 424/114; 260/245.2 T; 260/245.2 R; 514/368
[58] Field of Search ................ 260/245.2 T, 245.2 R; 424/270, 114

[56] References Cited

U.S. PATENT DOCUMENTS

| | | | |
|---|---|---|---|
| 3,487,079 | 12/1969 | Sheehan | 260/245.2 R X |
| 4,207,323 | 6/1980 | Beattie et al. | 424/270 |
| 4,234,579 | 3/1980 | Barth | 424/246 |
| 4,237,051 | 2/1980 | McCombie | 260/245.2 R |
| 4,244,951 | 1/1981 | Bigham | 424/250 |
| 4,260,598 | 4/1981 | Barth | 424/114 |
| 4,287,181 | 9/1981 | Kellogg | 424/271 X |
| 4,309,347 | 1/1982 | Bigham | 260/245.2 R |
| 4,342,693 | 8/1982 | Sakamoto | 549/229 |
| 4,342,768 | 8/1982 | Kellogg | 424/250 |
| 4,342,772 | 8/1982 | Godtfredsen et al. | 424/271 |
| 4,416,891 | 11/1983 | Sakamoto et al. | 260/245.2 R |

FOREIGN PATENT DOCUMENTS 2053220  2/1981  United Kingdom .

OTHER PUBLICATIONS

Sheehan et al., J. Org. Chem., 42, pp. 4045–4048, (1977).
Clayton et al., J. Med. Chem., 19, pp. 1385–1389, (1976).

Primary Examiner—Nicholas S. Rizzo
Attorney, Agent, or Firm—Charles J. Knuth; Albert E. Frost; Robert K. Blackwood

[57] ABSTRACT 6-alpha- and 6-beta-(Aminomethyl)penicillanic acid, 1,1-dioxide esters which are hydrolyzable under physiological conditions, particularly those wherein the ester radical is 1H-isobenzofuran-3-on-1-yl or (5-methyl-1,3-dioxol-2-on-4-yl)methyl, and an improved process and intermediates used in their synthesis.

17 Claims, No Drawings

6-(AMINOMETHYL)PENICILLANIC ACID 1,1-DIOXIDE ESTERS AND INTERMEDIATES THEREFOR

CROSS REFERENCE TO RELATED APPLICATION

This application is a continuation-in-part of co-pending application Ser. No. 501,451, filed June 6, 1983, now abandoned.

BACKGROUND OF THE INVENTION

The present invention provides an alternative process and intermediates for the synthesis of 6-alpha-and 6-beta-(aminomethyl)penicillanic acid 1,1-dioxide esters which are hydrolyzable under physiological conditions. This process is of particular value in the synthesis of those hydrolyzable esters, such as the (5-methyl-1,3-dioxol-2-on-4-yl)methyl,

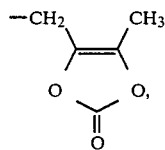

and the 1H-isobenzofuran-3-on-1-yl,

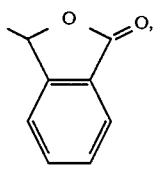

esters, which tend to be lost in alternative processes which employ a hydrogenolysis step.

My co-pending U.S. patent application Ser. No. 434,371, filed Oct. 21, 1982 discloses compounds of the formulae

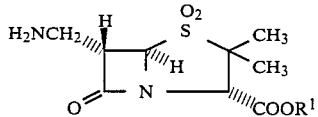

and

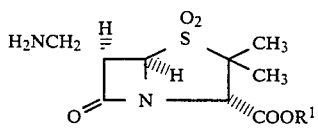

wherein $R^1$ is hydrogen or a conventional ester forming radical which is hydrolyzable under physiological conditions. That application also discloses the utility of these compounds, particularly as beta-lactamase inhibitors used in therapy in combination with beta-lactam antibiotics. That earlier application also describes a process and intermediates for the ester compounds (I) and (II) which (like the present process) employs the acid compounds (I) and (II) [$R^1$=H] as starting material, but (unlike the present process) includes a hydrogenolysis step.

My co-pending application, Ser. No. 501,476, filed June 6, 1983 describes an alternative process for the above 6-alpha-(aminomethyl)penicillanic acid 1,1-dioxide esters; and the co-pending application of Pirie et al., Ser. No. 501,475, also filed June 6, 1983 describes yet another process for both of the above 6-alpha- and 6-beta-(aminomethyl)penicillanic acid 1,1-dioxide esters.

In all of the above cited processes, those in vivo hydrolyzable groups which do not tend to be removed under the hydrogenolysis conditions used in their preparation are preferred. Thus the present process is particularly advantageous in now allowing the efficient synthesis of in vivo hydrolyzable esters which are susceptible to such hydrogenolysis, in particular the efficient synthesis of 1H-isobenzofuran-3-on-1-yl and (5-methyl-1,3-dioxol-2-on-4-yl)methyl 6-(aminomethyl)penicillanate 1,1-dioxides.

Other compounds previously reported as beta-lactamase inhibitors useful in combination with beta-lactam antibiotics for the treatment of bacterial infections include penicillanic acid 1,1-dioxide and esters thereof readily hydrolyzable in vivo (Barth, U.S. Pat. No. 4,234,579); the bis-methanediol ester of sulbactam (Bigham, U.S. Pat. No. 4,309,347); various 6-beta-(hydroxymethyl)penicillanic acid 1,1-dioxides and esters thereof (Kellogg, U.S. Pat. No. 4,287,181); and 6-beta-(aminomethyl)penicillanic acid (McCombie, U.S. Pat. No. 4,237,051). Talampicillin (USAN generic name), the 1H-isobenzofuran-3-on-1-yl ester of ampicillin (Clayton et al., J. Med. Chem., 19, pp. 1385–1390, 1976), and (5-methyl-1,3-dioxiol-3-on-4-yl)methyl ester of ampicillin (Sakamoto et al., U.S. Pat. No. 4,342,693) exemplify those in vivo hydrolyzable ester radicals of particular interest in the present case. Above cited Clayton et al. also illustrates various crotonolactonyl and butyrolactonyl esters of ampicillin as in vivo hydrolyzable esters.

U.K. Pat. No. 2,053,220, published Feb. 4, 1981, broadly discloses beta-lactamase inhibiting compounds of the formula

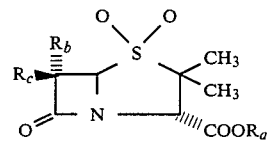

The definitions of $R_a$, $R_b$ and $R_c$ define literally an infinite number of compounds. These definitions, by appropriate selection of $R_a$, $R_b$ and $R_c$, may possibly define the 6-alpha-(aminomethyl)penicillanic acid 1,1-dioxides of present interest. No specific method for preparation of these compounds is present in the disclosure of this U.K. application, and there is no hint or suggestion that from among the infinity of compounds proposed, the present aminomethyl compounds are preferred compounds, possessing the particularly highly potent beta-lactamase inhibitory activity which we have determined for them.

SUMMARY OF THE INVENTION

The present invention relates to a process for the preparation of an ester of 6-alpha- or 6-beta-(aminomethyl)penicillanic acid 1,1-dioxides which are hydrolyzable under physiological conditions, i.e., the above compounds of the formula (I) or (II) wherein $R^1$ is an in vivo hydrolyzable ester group. Particularly valuable compounds of this class, now efficiently available by the present process, are the compounds of the formula

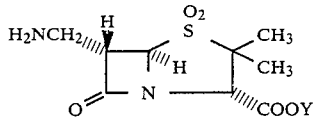 (III)

and

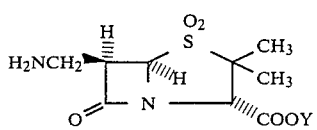 (IV)

wherein Y is

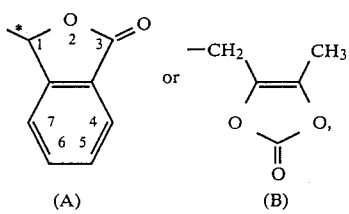

incuding the pharmaceutically acceptable acid addition salts thereof. The most preferred compounds are the 6-alpha compounds, of the formula (III), with either value of Y.

It will be evident to those skilled in the art that there are equivalent, conventional in vivo hydrolyzable groups, such as radical (A) substituted in the 1 position with alkyl or aryl or at aromatic 4- to 7-positions with alkyl, alkoxy or halo (see Clayton et al., cited above); radical (B) wherein the methyl group is replaced by hydrogen or an aryl group, or the methylene group and the methyl group are bridged by a divalent methylene or ethylene group (see U.S. Pat. No. 4,342,693 cited above); a crotonyl radical of the type:

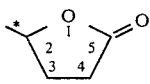

optionally substituted at the 3 and/or 4-position with lower alkyl (see Clayton et al. and Murakami et al., U.S. Pat. No. 3,951,954); or a radical of the type:

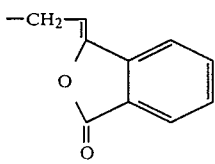 (D)

where again the aromatic ring is optionally substituted [see Sakamoto et al., Chem, Pharm. Bull., 31, 2698 (1983)].

As used in the above structural formula, the asterisk (*) denotes an asymmetric carbon atom. As those skilled in the art will know, present esters containing such groups will generally comprise a mixture of two diastereomeric isomers, which are generally separable based on their different physical properties, e.g., solubility or mobility on chromatography. When one particular diastereomer is desired, it is preferable to carry out the separation at the earliest possible stage in the synthesis, thus avoiding processing of undesired material.

The above-mentioned pharmaceutically-acceptable acid addition salts include, but are not limited to, those with hydrochloric acid, sulfuric acid, nitric acid, phosphoric acid, citric acid, maleic acid, succinic acid, benzenesulfonic acid, p-toluenesulfonic acid, 2-naphthalenesulfonic acid and methanesulfonic acid.

Valuable intermediates of the present invention are the protected amino beta-lactam compounds of the formulae

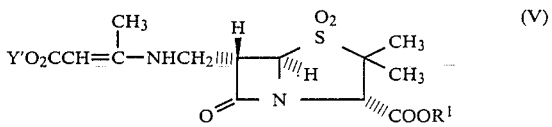 (V)

and

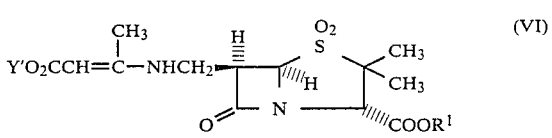 (VI)

wherein Y' is $(C_1-C_3)$alkyl and $R^1$ is hydrogen, or a conventional ester forming radical which is hydrolyzable under physiological conditions, and the cationic salts thereof when $R^1$ is hydrogen. Preferred compounds are generally of the formula (V). Those skilled in the art will recognize that the compounds (V) and (VI) can exist as geometric, cis/trans isomers. However, that isomerism (i.e., whether these compounds exist one way or the other or in both forms) is not an important feature of the present invention.

The intermediate compounds formed in the first stage of the present process are the salts of the acids (V) and (VI) wherein $R^1$ is hydrogen. The preferred salt is the tetrabutylammonium salt.

Those intermediate compounds (V) and (VI) which are formed in the second stage are those wherein $R^1$ is an ester forming radical which is hydrolyzable under physiological conditions. All reference herein to such esters concern those esters frequently referred to as "pro-drugs". Such esters are now as well-known and common in the penicillin art as pharmaceutically-acceptable salts. They are generally used to enhance oral absorption, but in any event are readily hydrolyzed in vivo to the parent acid, having beta-lactamase inhibitory activity.

Finally, the intermediates (V) and (VI) wherein $R^1$ represents a conventional in vivo hydrolyzable ester are converted to the corresponding ester of 6-alpha-and 6-beta-(aminomethyl)penicillanic acid, of the formulae (I) and (II) above, wherein $R^1$ is an ester group.

Preferred ester forming radicals are

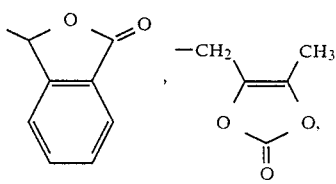

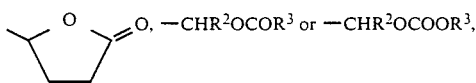

wherein $R^2$ is hydrogen or methyl and $R^3$ is $(C_1-C_6)$alkyl.

In terms of the present process, the more preferred radicals are

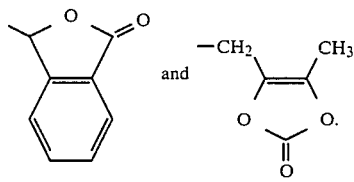

The preferred values of Y' are methyl or ethyl, especially methyl.

DETAILED DESCRIPTION OF THE INVENTION

The process providing the present intermediates and products is readily carried out. If not already in hand, the starting 6-alpha- or 6-beta-(aminomethyl)penicillanic acid, 1,1-dioxide is first converted to a cationic salt. The salt can be an inorganic salt such as that of an alkali or alkaline earth metal, or an organic salt such as that of a tertiary amine or a quaternary ammonium salt. The latter type salt is preferred, the tetrabutylammonium salt being most preferred. The required cationic salts are readily prepared by methods standard in the art. For example, the tetrabutylammonium salt is conveniently prepared by combining equivalent amounts of the penicillanic acid derivative and tetrabutylammonium hydroxide in a mxiture of water and a reaction inert immiscible organic solvent such as chloroform. The organic layer is separated, dried (with a drying agent or azeotropically) and the salt recovered by evaporation to dryness.

As employed herein, the expression "reaction-inert solvent" refers to a solvent which does not interact with reactants or products in a manner which adversely affects the yield of the desired product.

The above salts are then reacted with at least one equivalent of a $(C_1-C_3)$alkyl acetoacetate, conveniently methyl acetoacetate, in a reaction inert solvent at 10°–70° C. It is preferred to use an excess of the acetoacetate ester, in order to faciliate complete reaction, and indeed the ester itself can serve as solvent for the reaction. In this manner, intermediate enamine compounds of the formula (V) and (VI) wherein $R^1$ is hydrogen in the form of a cationic salt are produced. Water formed in this process is generally removed either by use of a drying agent or by azeotropic distillation, e.g., with benzene.

The above enamine, still as the salt (preferably the tetrabutylammonium salt) is then reacted under typical nucleophilic displacement conditions with a compound of the formula Z—$R^7$ wherein $R^7$ corresponds to the in vivo hydrolyzable ester radical defined above for $R^1$ and Z is a nucleophilically displaceable group such as mesylate or halide (preferably bromide or chloride). When the salt is a quaternary salt such as the tetrabutylammonium salt, the nucleophilic displacement occurs rapidly under mild conditions, e.g. at 0°–50° C., conveniently at ambient temperature, in a reaction inert solvent such as acetone. In this manner, intermediate enamine compounds (V) and (VI) wherein $R^1$ is an in vivo hydrolyzable ester are formed. They are isolated by standard methods of precipitation, chromatography and/or evaporation.

Finally the above enamine esters are hydrolyzed under mildly acidic conditions in an aqueous solvent, comprising simply water or water and a water miscible or immiscible reaction inert organic solvent; at 0°–50° C., conveniently at ambient temperature. The two phase system of water and ethyl acetate at ambient temperature represents particularly suitable conditions. Conveniently, one equivalent of a strong acid such as HCl or a sulfonate salt is used, and the product is isolated in the form of that acid addition salt.

The 6-alpha- and 6-beta-(aminomethyl)penicillanic acid 1,1-dioxides, required as starting materials, are of the formulae (I) and (II) above, wherein $R^1$ is hydrogen. They are prepared according to methods dscribed in the various patent applications cited above. These methods are also illustrated in specific preparations below.

Some of the compounds of the formulae (I) and (II), generally those wherein $R^1$ is hydrogen, have in vitro antibacterial activity. Such activity is demonstrated by measuring the minimum inhibitory concentrations (MIC's) in mcg/ml against a variety of microorganisms. The procedure which is followed is the one recommended by the International Collaborative Study on Antibiotic Sensitivity Testing (Ericcson and Sherris, *Acta. Pathologica et Microbiologia Scandinav,* Supp. 217, Section B: 64–68 [1971]), and employs brain heart infusion (BHI) agar and the inocula replicating device. Overnight growth tubes are diluted 100 fold for use as the standard inoculum (20,000–10,000 cells in approximately 0.002 ml are placed on the agar surface; 20 ml of BHI agar/dish). Twelve 2 fold dilutions of the test compound are employed, with initial concentration of the test drug being 200 mcg/ml. Single colonies are disregarded when reading plates after 18 hours at 37° C. The susceptibility (MIC) of the test organism is accepted at the lowest concentration of compound capable of producing complete inhibition of growth as judged by the naked eye.

Those compounds of the formulae (I) and (II) having said in vitro antibacterial activity are thus useful as industrial antimicrobials, for example in water treatment, slime control, paint preservation and wood preservation, as well as for topical application as a disinfectant. In the case of use of these compounds for topical application, it is often convenient to admix the active ingredient with a nontoxic carrier, such as vegetable or mineral oil or an emollient cream. Similarly, it can be dissolved or dispersed in liquid diluents or solvents such as water, alkanols, glycols or mixtures thereof. In most instances it is appropriate to employ concentrations of the active ingredient of from about 0.1 percent to about 10 percent by weight, based on total composition.

As indicated above, the compounds of the formulae (I) and (II) are of more particular value as potent inhibitors of microbial beta-lactamases. By this mechanism they increase the antibacterial effectiveness of beta-lactam antibiotics (penicillins and cephalosporins against many microorganisms, particularly those which produce a beta-lactamase. The ability of the said compounds of the formula (I) or (II) to increase the effectiveness of a beta-lactam antibiotic can be appreciated by reference to experiments in which the MIC values of the antibiotic alone, and a compound of the formula (I) and (II) (having $R^1$ as hydrogen) alone, are determined. These MIC's are then compared with the MIC values obtained with a combination of the given antibiotic and the compound of the formula (I) or (II), wherein $R^1$ is hydrogen. When the antibacterial potency of the combination is significantly greater than would have been predicted from the potencies of the individual compounds, this is considered to constitute enhancement of activity. The MIC values of combinations are measured using the method described by Barry and Sabath in "Manual of Clinical Microbiology", edited by Lenette, Spaulding and Truant, 2nd Edition, 1974, American Society for Microbiology.

The compounds of the formulae (I) and (II) also enhance the antibacterial effectiveness of beta-lactam antibiotics in vivo, the esters functioning by hydrolysis to the fully active acids under such physiological conditions. The ability of the compounds of formulae (I) and (II) to enhance the effectiveness of a beta-lactam antibiotic against beta-lactamase producing bacteria makes them valuable for coadministration with beta-lactam antibiotics in the treatment of bacterial infections in mammals, particularly man. In the treatment of a bacterial infection, the compound of the formula (I) or (II) can be comingled with the beta-lactam antibiotic, and the two agents thereby administered simultaneously. Alternatively, the compound of the formula (I) or (II) can be administered as a separate agent during a course of treatment with a beta-lactam antibiotic. In some instances it will be advantageous to pre-dose the subject with the compound of the formula (I) or (II) before initiating treatment with a beta-lactam antibiotic.

When using a compound of formula (I) or (II) to enhance the effectiveness of a beta-lactam antibiotic, a mixture of (I) or (II) with the beta-lactam antibiotic is administered preferably in formulation with standard pharmaceutical carriers or diluents. A pharmaceutical composition comprising a pharmaceutically acceptable carrier, a beta-lactam antibiotic and a compound of formula (I) or (II) will normally contain from about 5 to about 80 percent of the pharmaceutically acceptable carrier by weight.

When using the compounds of formula (I) or (II) in combination with another beta-lactam antibiotic, said compounds can be administered orally or parenterally, i.e. intramuscularly, subcutaneously or intraperitoneally. Although the prescribing physician will ultimately decide the dosage to be used in a human subject, the ratio of the daily dosages of the compounds of formula (I) or (II) and the beta-lactam antibiotic will normally be in the range from about 1:3 to 3:1 by weight. Additionally, when using the compounds of formula (I) or (II) in combination with another beta-lactam antibiotic, the daily oral dosage of each component will normally be in the range from about 10 to about 200 mg per kilogram of body weight and the daily parenteral dosage of each component will normally be about 10 to about 40 mg per kilogram of body weight. These daily doses will usually be divided. In some instances, the prescribing physician will determine that dosages outside these limits are necessary.

As will be appreciated by one skilled in the art, some beta-lactam compounds are effective when administered orally or parenterally, while others are effective only when administered by the parenteral route. When a compound of formula (I) or (II) is to be used simultaneously (i.e. comingled) with a beta-lactam antibiotic which is effective only on parenteral administration, a combination formulation suitable for parenteral use will be required. When a compound of formula (I) or (II) is to be used simultaneously (comingled) with a beta-lactam antibiotic which is effective orally or parenterally, combinations suitable for either oral or parenteral administration can be prepared. Additionally, it is possible to administer preparations of the compounds of formula (I) or (II) orally, while at the same time administering a further beta-lactam antibiotic parenterally; and it is also possible to administer preparations of the compounds of formula (I) or (II) parenterally, while at the same time administering the further beta-lactam antibiotic orally.

The present invention is illustrated by the following examples. However, it should be understood that the invention is not limited to the specific details of these examples. Unless otherwise specified, all operations were carried out at ambient temperatures; all temperature are in °C., all drying of solutions was over anhydrous $Na_2SO_4$; all solvent evaporations were carried out in vacuo; and all pnmr (proton nuclear magnetic resonance) spectra were at 60 MHz. The abbreviations DMF, TEA, THF and DMSO are used, respectively, for N,N-dimethylformamide, triethylamine, tetrahydrofuran and dimethylsulfoxide.

EXAMPLE 1

Tetrabutylammonium
6-alpha-(Aminomethyl)penicillanate 1,1-Dioxide

To a solution of 6-alpha-(aminomethyl)penicillanic acid 1,1-dioxide (0.524 g, 2.0 mmoles) in 50 mL $CHCl_3$ was added tetrabutylammonium hydroxide (1.3 mL of 1.527N, 2.0 mmoles). After stirring 5 minutes, the organic layer was separated, dried and evaporated to yield title product as an oil, 0.806 g.

Alternatively, to 15.7 g (0.06 moles) of the same starting material in 450 mL $CH_2Cl_2$ at 0°–5° C. was added 39.3 mL (0.06 moles) of the same hydroxide over 5 minutes. The cooling bath was removed and after stirring 5 minutes, title product (30.2 g) isolated according to the method of the preceding paragraph.

EXAMPLE 2

Tetrabutylammonium
6-alpha-[(2-methoxycarbonyl-1-methylvinyl)-aminomethyl]penicillanate 1,1-Dioxide Title product of the preceding example (0.806 g) was dissolved in 1 mL methyl acetoacetate and heated at 60° for 15 minutes under $N_2$. The mixture was cooled, diluted with 75 mL benzene and concentrated in vacuo to yield title product, all of which was used directly in the next step.

Alternatively, title product of the preceding example (30.2 g, about 0.06 moles) was combined with 30 ml of methyl acetoacetate and stirred for 5 minutes at room temperature. Benzene (150 mL) was added and the mixture striped in vacuo to an oil, a step which was twice repeated. The resulting oil was triturated 3 times with 200 mL portions of hexane, decanting each time with final drying of the oil under high vacuum. The yield of title product was 36.06 g.

EXAMPLE 3

(5-Methyl-1,3-dioxol-2-on-4-yl)methyl 6-alpha-[(2-Methoxycarbonyl-1-methylvinyl)aminomethyl]penicillaneat 1,1-Dioxide The entire batch of title product prepared according to the first paragraph of the preceding example in 20 mL of acetone was added to a solution of (5-methyl-1,3-dioxol-2-on-4-yl)methyl bromide (0.772 g., 4.0 mmoles) in 10 mL of acetone. After stirring 0.5 hour, the reaction mixture was concentrated to an oil, dissolved in $CHCl_3$ and filtered through 30 g silica gel with $CHCl_3$ eluant. Fractions of 30 mL were collected—fractions 3-6 on evaporation gave title product as a foam, 0.38 g; tlc $R_f$ 0.2 (7:3 $CHCl_3$:ethyl acetate).

EXAMPLE 4

(5-Methyl-1,3-dioxol-2-on-4-yl)methyl 6-alpha-(Aminomethyl)penicillanate 1,1-Dioxide p-Toluenesulfonate Title product of the preceding example (0.38 g, 0.807 mmole) was dissolved in 20 mL of water saturated ethyl acetate. p-Toluenesulfonic acid monohydrate (0.153 g, 0.807 mmole) in 10 mL ethyl acetate was added dropwise over 5 minutes. After stirring 0.5 hour under $N_2$, the mixture was concentrated to an oil, 0.53 g, which crystallized from $CHCl_3$, 0.22 g; pnmr/DMSO-$d_6$/TMS/delta (ppm): 1.34 (3H, s), 1.51 (3H, s), 2.17 (3H, s), 2.31 (3H, s), 3.40 (2H, m), 3.94 (1H, m), 4.53 (1H, s), 5.13 (3H, m), 7.30 (4H, q), 8.03 (3H, br. s).

By the procedures of examples 1–4, 6-beta-(aminomethyl)penicillanic acid is converted to (5-methyl-1,3-dioxol-2-on-4-yl)methyl 6-beta-(aminomethyl)penicillanate 1,1-dioxide p-toluenesulfonate.

EXAMPLE 5

1H-Isobenzofuran-3-on-1-yl 6-alpha-[(2-methoxycarbonyl-1-methylvinyl)aminomethyl]penicillanate 1,1-Dioxide By the procedures of examples 1 and 2,6-alpha-(aminomethyl)penicillanic acid 1,1-dioxide (2.62 g) was converted to example 2 title product, 4.3 g, as an oil. The latter was dissolved in 50 mL acetone and mixed with 1H-isobenzofuran-3-on-1-yl bromide (3-bromophthalide) (1.52 g, 7.15 mmoles) in 20 mL acetone. After stirring 2 hours, the mixture was concentrated and the residue triturated to yield crude product as and oil, 4.3 g. The latter was filtered on 60 g silica gel, eluting with 300 mL $CHCl_3$. The eluant was concentrated to yield title product as a foam, 0.8 g; tlc $R_f$0.5 (9:1 $CHCl_3$:ethyl acetate.

By the same procedure, chloromethylpivalate (using a reaction time of 20 hours) and alpha-chlorodiethylcarbonate (using a reaction time of 36 hours) are converted to pivaloyloxymethyl and 1-(ethoxycarbonyloxy)ethyl 6-alpha-[(2-methoxycarbonyl-1-methylvinyl)aminomethyl]penicillanate 1,1-dioxide, respectively.

EXAMPLE 6

1H-Isobenzofuran-3-on-1-yl 6-alpha-(Aminomethyl)penicillanate 1,1-Dioxide p-Toluenesulfonate By the procedure of example 4, title product of the preceding example (0.8 g, 1.62 mmoles) was converted to present tilte product, initially isolated as a foam. The foam was triturated with 100 mL of ether and scratched to solidfy, 0.69 g; pnmr/CDCl$_3$/TMS/delta (ppm): 1.40 (3H, s), 1.58 (3H, s), 1.95 (3H, s), 2.21 (3H, s), 3.60 (3H, s), 3.73 (3H, m), 4.40 (2H, m), 4.52 (1H, s), 5.00 (2H, s).

By the same procedure, the other esters of the preceding example are converted to pivaloyloxymethyl 6-alpha-(aminomethyl)penicillanate 1,1-dioxide and 1-(ethoxycarbonyloxy)ethyl 6-alpha-(aminomethyl)-penicillanate 1,1-dioxide.

EXAMPLE 7

1H-Isobenzofuran-3-on-1-yl 6-alpha-(Aminomethyl)penicillanate 1,1-Dioxide Hydrochloride Title product of example 2 (36 g) was dissolved in 300 mL acetone, a solution of 1H-isobenzofuran-3-on-1-yl bromide (12.78 g, prepared according to Preparation 14) in 150 mL acetone was added, and the mixture stirred for 18 hours at room temperature to yield a solution of the title product of example 5.

The solution was immediately cooled to 0°–5° C., and 60 mL of 1N HCl added over a 5 minute period. After stirring at 0°–5° C. for 1.5 hours, crystalline title product as a single diastereoisomer (which had begun to form after about 20 minutes) was recovered by filtration with acetone wash, 3.3 g., m.p. 179°–180° C. (dec.). A second crop was obtained by concentrating the mother liquor in vacuo, diluting with 450 mL $CHCl_3$ and 300 ml $H_2O$, stirring 30 minutes, and filtering with acetone wash, 2.4 g., m.p. 179°–180 ° C. (dec.). The two crops were combined and dried in vacuo for 20 hours over $P_2O_5$, 6.7 g., m.p. 179°–180° C. (dec.).

Anal. Calcd. for $C_{17}H_{18}O_7N_2S.HCl.H_2O$:
C, 45.48; H, 4.71; N, 6.24.
Found: C, 45.73; H, 4.93; N, 6.14.

pnmr/DMSO-$d_6$/TMS/delta (ppm): 1.43 (3H, s, 2-C$\underline{H}_3$), 1.49 (3H, s, 2-C$\underline{H}_3$), 3.36 (2H, m, N-C$\underline{H}_2$), 3.97 (1$\underline{H}$, m, 6-H), 4.83 (1$\underline{H}$, s, 3-H), 5.43 (1H, d, $\overline{J}$=2Hz, 5-$\underline{H}$), 7.63 (1H, s, benzylic-C$\underline{H}$), 7.76–7.99 (4H, multiplet, aromatic).

PREPARATION 1

6-alpha-Bromopenicillanic Acid 1,1-Dioxide

To 6,6-dibromopenicillanic acid 1,1-dioxide (117.3 g, 0.3 mole), stirring in a mixture of $H_2O$ (600 mL) and ethyl acetate (400 mL), was added in portions NaHCO$_3$(75.6 g, 0.9 mole) and then NaHSO$_3$ (37.5 g, 0.36 mole). After stirring 1 hour, the pH was adjusted from 3.7 to 1.5 with concentrated HCl. The aqueous layer was separated and extracted 1×400 mL with fresh ethyl acetate. The combined organic layers were backwashed with brine, dried and evaporated to yield title product as a solid; 72 g (76.7%); m.p. 136°–137°, pnmr/D$_2$O-NaHCO$_3$/delta: 1.48 (s, CH$_3$), 1.62 (s, CH$_3$), 4.28 (s, C.3-H), 5.12 (d, J=1.7, C.6-H), 5.37 (d, J=1.7, C.5-H).

PREPARATION 2

Benzyl 6-alpha-Bromopenicillanate 1,1 -Dioxide

To title product of the preceding preparation (24.3 g, 0.0779 mole) in 75 mL DMF was added TEA (7.87 g, 0.0779 mole) and benzyl bromide (13.32 g, 0.0779 mole). The mixture was stirred 16 hours, poured into 250 mL $H_2O$ and extracted 2×200 mL ethyl acetate. The combined organic layers were washed with saturated NaHCO$_3$, $H_2O$ and brine, dried, evaporated to dryness and the residue crystallized from ethyl acetate/hexane; 28.8 g (92%); m.p. 72°–74 °; pnmr/CDCl$_3$/delta (ppm): 1.27 (s, CH$_3$), 1.53 (s, CH$_3$), 4.53 (s, C.3H), 4.8 (d, J=1.7, C.6-H), 5.27 (d, J=1.7, C.5-H), 5.3 (d, CH$_2$), 7.5 (s, C$_6$H$_5$).

PREPARATION 3

Benzyl 6,6-Dibromopenicillanate 1,1-Dioxide

By the method of the preceding preparation, 6,6-dibromopenicillanic acid 1,1-dioxide (39.2 g) was converted to present title product; 37 g (77%); m.p. (crude) 134°–136°, (recrystallized) 146°–148°; pnmr/CDCl$_3$/delta (ppm): 1.27 (s, CH$_3$), 1.55 (s, CH$_3$), 4.62 (s, C.3-H), 5.13 (s, C.5-H), 5.3 (d, CH$_2$), 7.46 (s, C$_6$H$_5$).

PREPARATION 4

Benzyl 6-alpha-(Methoxyaminomethyl)penicillanate 1,1-Dioxide

Title product of preparation 2 (4.02 g, 0.01 mole) in dry THF (75 mL) was stirred at −75° under N$_2$. Methylmagnesium bromide (2.98 M in ether; 3.35 mL, 0.01 mole) was added dripwise over 3 minutes maintaining less than −67°. Formaldehyde O-methyloxime (0.59 g, 0.01 mole) in THF (25 mL) was cooled to −70°, and BF$_3$ etherate (1.42 g, 0.01 mole) added. The resulting solution of complex was added to the above Grignard solution at −70° and the mixture stirred 1 hour at −70° to −76°. Acetic acid (2 mL) was added over 3 minutes and the reaction mixture warmed and evaporated. The residue was distributed in 50 mL H$_2$O and 100 mL ethyl acetate. The aqueous layer was at pH 1.7. The ethyl acetate layer was separated, washed with saturated NaHCO$_3$ (75 mL) and then brine, dried and evaporated to a gum (3.58 g). Chromatography on silica gel, eluting with 4:1 CHCl$_3$:ethyl acetate gave purified title product as a gum; 1.88 g; tlc R$_f$0.3 (3:1 CHCl$_3$: ethyl acetate); pnmr/CDCl$_3$/delta (ppm) 1.3 (s, CH$_3$ ), 1.57 (s, CH$_3$), 3.47 (m, NCH$_2$), 3.58 (s, OCH$_3$), 4.0 (m, C.6-H), 4.52 (s, C.3-H), 4.82 (d, J=1.7, C.5-H), 5.33 (d, OCH$_2$), 7.57 (s, C$_6$H$_5$).

PREPARATION 5

Benzyl 6-beta-Bromo-6-alpha-(Methoxyaminomethyl)penicillanate 1,1-Dioxide

By the method of the preceding preparation title product of preparation 3 (26.17 g, 0.0544 mole) was converted to present title product (27.7 g of crude), purified by silica gel chromatography using 17:3 CHCl$_3$:ethyl acetate as eluant; 10.7 g (42.5%); m.p. 107°–109°; tlc R$_f$0.52 (17:3 CHCl$_3$:ethyl acetate); pnmr (250 MHz)/CDCl$_3$/delta (ppm): 1.28 (s, CH$_3$), 1.59 (s, CH$_3$), 3.54 (s, OCH$_3$), 3.6 (octet, NCH$_2$), 4.54 (s, C.3-H), 4.95 (s, C.5-H), 5.26 (q, OCH$_2$), 5.99 (q, NH), 7.39 (s, C$_6$H$_5$).

PREPARATION 6

Benzly 6-beta-(Methoxyaminomethyl)penicillanate 1,1-Dioxide

Title product of the preceding preparation (26 g, 0.056 mole) and tri(n-butyl)tin hydride (49.6 g, 0.17 mole) were combined in 250 mL benzene and the mixture refluxed gently for 2 hours. The reaction mixture was evaporated and the residue extracted with hexane, and then dissolved in CH$_3$CN. The CH$_3$CN solution was washed with fresh hexane, separated and evaporated to a gum. The gum was chromatographed on silica gel with 4:1 CHCl$_3$:ethyl acetate as eluant to yield present, purified title product as an oil which crystallized on standing; 11.4 g; m.p. 99°–102°; tlc R$_f$0.38 (17:3 CHCl$_3$:ethyl acetate); pnmr/CDCl$_3$/delta (ppm): 1.27 (s, CH$_3$), 1.52 (s, CH$_3$), 3.6 (s, OCH$_3$), 3.67 (m, NCH$_2$), 4.55 (s, C.3-H), 4.75 (d, J=4, C.5-H), 5.3 (d, OCH$_2$), 7.53 (s, C$_6$H$_5$).

PREPARATION 7

Benzyl 6-alpha-(Methoxyaminomethyl)penicillanate 1,1-Dioxide

Title product of the preceding preparation (5.73 g, 0.015 mole) was stirred in 125 mL CH$_2$Cl$_2$, 1,5-diazabicyclo[4.3.0]nonene (1.86 g, 0.015 mole) was added, followed after 1 minute of stirring by CH$_3$CO$_2$H (3.6 g, 0.06 mole) and after 2 more minutes of stirring, 100 mL of H$_2$O. The organic layer was separated, washed with 50 mL saturated NaHCO$_3$ and then 50 mL brine, dried and evaporated to yield title product as a gum; 5.35 g; pnmr identical with the chromatographed product of preparation 4.

PREPARATION 8

6-alpha-(Aminomethyl)-penicillanic Acid 1,1-Dioxide

Title product of preparations 4 and 7 (0.5 g, 0.0013 mole) in 3:1 THF:H$_2$O (20 mL) was hydrogenated over 500 mg of Raney nicket catalyst under 4 atmospheres of hydrogen for 2 hours, monitoring by tlc. The reaction was filtered and filtrate evaporated to yield title product as a white solid; pnmr/D$_2$O/delta (ppm): 1.42 (s, CH$_3$), 1.57 (s, CH$_3$), 3.55 (m, CH$_2$), 3.97 (m, C.6-H), 4.22 (s, C.3-H), 4.98 (d, J=1.7, C.5-H); tlc R$_f$0.3 (6:1:1 acetone:CH$_3$CO$_2$H:H$_2$O).

PREPARATION 9

6-beta-(Aminomethyl)-penicillanic Acid 1,1-Dioxide

By the method of the preceding preparation, title product of preparation 6 (130 mg) in 25 mL 3:2 THF:H$_2$O in the presence of 200 mg Raney nickel was converted to present title product; tlc R$_f$0.3 (6:1:1 acetone: CH$_3$CO$_2$H:H$_2$O); pnmr/D$_2$O/delta (ppm) includes 1.47 (s, CH$_3$), 1.6 (s, CH$_3$), 3.81 (m, CH$_2$), 4.43 (s, C.3-H), 5.33 (d, J=4, C.5-H).

PREPARATION 10

Benzyl 6-alpha-(Ethoxyaminomethyl)penicillanate 1,1-Dioxide

Title product of preparation 2 (80.6 g, 0.20 mole) in 800 mL dry THF was cooled to −70°. CH$_3$MgBr (69 mL or 2.9 M in ether, 0.02 mole) was added over 40 minutes, maintaining temperature by the rate of addition. Meanwhile, in a separate flask formaldehyde O-ethyloxime (16.3 g, 0.22 mole) and BF$_3$.etherate (31.2 g, 26.9 mL, 0.22 mole) in 100 mL dry THF was cooled to −70°. As soon as CH$_3$MgBr addition was complete, the latter solution was added all at once to the former solution. The temperature, which rose to −60°, was reduced to −70° and the mixture stirred 1 hour. CH$_3$CO$_2$H (28.6 mL, 0.5 mole) was added over 15 minutes, maintaining less than −60°. The mixture was evaporated to a foam which was distributed between 700 mL CH$_2$Cl$_2$ and 400 H$_2$O the pH adjusted to 8 with saturated NaHCO$_3$. The resulting emulsion was broken by the addition of ethyl acetate. The organic layer was separated, washed with brine, dried and evaporated to an oil. The oil was chromatographed on a short silica gel column, first eluting less polar impurities with CHCl₃ and then eluting crude product with ethyl acetate. The latter was isolated as a second oil, which was rechromatographed on 500 g silica gel eluted with 1:19 ethyl acetate:CHCl₃, monitored by tlc. Pure product fractions were combined and evaporated to yield purified title product as an oil, 13.9 g, tlc R_f 0.4 (4:1 CHCl₃:ethyl acetate).

PREPARATION 11

6-alpha-(Aminomethyl)penicillanic Acid 1,1-Dioxide

By the method of preparation 8, title product of the preceding preparation (13.9 g) was hydrogenated over Raney nickel. After removing the catalyst by filtration, THF was removed by evaporation and impurities extracted away with ethyl acetate, forming a clean, aqueous solution of title product; tlc R_f 0.3 (6:1:1 acetone:CH₃CO₂H:H₂O). Title product is isolated by further evaoration or freeze drying to yield product identical to that of preparations 8 and 13.

PREPARATION 12

Benzyl 6-alpha-(Benzyloxycarbonylaminomethyl)penicillanate 1,1-Dioxide

Benzyl 6-alpha-bromopenicillanate 1,1-dioxide (0.804 g, 2.0 mmoles) in 30 mL dry THF was cooled to −κ°. Ethereal CH₃MgBr (2.8 M, 1.43 mL, 4.0 mmoles) was added over 3 minutes and stirring continued for 7 minutes at −78°, forming the corresponding 6-alpha-bromomagnesium Grignard reagent. A solution of benzyl N-(acetoxymethyl)carbamate (0.57 g, 2.0 mmole) in 5 mL dry THF was then added. After stirring 5 minutes at −78°, the reaction mixture was quenched by the addition of 0.5 mL CH₃CO₂H, the solvent evaporated and the residue taken up in CHCl₃, washed with H₂O, saturated NaHCO₃ and brine, dried and evaporated to a viscous oil (1.1 g). The oil was chromatographed on 40 g silica gel eluting with 1:19 ethyl acetate: chloroform in 20 mL fractions. Fractions 5–8 were combined, evaporated to an oil (0.55 g) which was crystallized by scratching in 10 mL ether; 0.32 g; pnmr/CDCl₃/delta/TMS 1.20 (3H, s), 1.49 (3H, s), 3.65 (3H, m), 4.32 (1H, s), 4.59 (1H, m), 5.07 (2H, s), 5.14 (2H, q), 5.30 (1H, br), 7.32 (10H, s).

PREPARATION 13

6-alpha-(Aminomethyl)penicillanic Acid 1,1-Dioxide

Title product of preceding preparation (1.7 g), THF (35 mL), H₂O (35mL) and 10% Pd/C (1.7 g) were combined and hydrogenated at 50 psig for 1 hour. Catalyst was recovered by filtration and THF removed from the filtrate in vacuo. The aqueous layer was washed with 30 mL ethyl acetate, and the aqueous layer concentrated to yield crystalline title product; 0.7 g; pnmr/250 MHz/D₂O/DSS 1.44 (3H, s), 1.59 (3H, s), 3.63 (2H, d, J=5.5 Hz), 4.07 (1H, td, J=2, 5.5 Hz), 4.31 (1H, s), 5.06 (1H, d, J=2).

PREPARATION 14

1H-Isobenzofuran-3-on-1-yl Bromide

1H-Isobenzofuran-3-one (40.2 g, 0.3 moles), N-bromosuccinimide (53.4 g., 0.03 moles) and azobisisobutyronitrile (1g) were combined in 500 mL of CCl₄ and refluxed under nitrogen for 2 hours. The reaction mixture was cooled to room temperature, filtered and the filtrate concentrated in vacuo to a solid residue. The latter was crystallized from cyclohexane to yield title product, 34.5 g., m.p. 78°–80° C.

I claim:

1. A beta-lactam ester of the formula

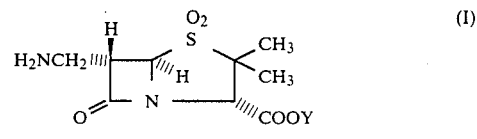

or

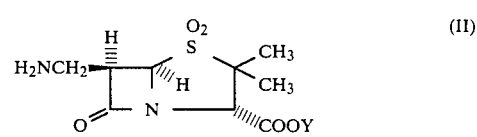

wherein Y is

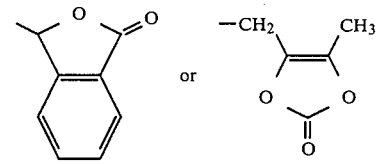

or a pharmaceutically acceptable acid addition salt thereof.

2. A compound of claim 1 of the formula (I).

3. The compound of claim 2 wherein Y is

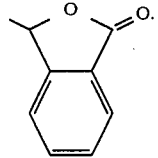

4. The compound of claim 2 wherein Y is

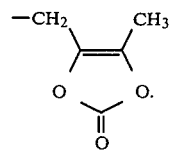

5. A pharmaceutical composition fore treating bacterial infections which comprises an antibacterially effective amount of a compound of claim 1 and a conventional beta-lactam antibiotic in a weight ratio of 1:3 to 3:1.

6. A pharmaceutical composition for treating bacterial infections which comprises an antibacterial effective amount of the compound of claim 3 and a conventional beta-lactam antibiotic in a weight ratio of 1:3 to 3:1.

7. A pharmaceutical composition for treating bacterial infections which comprises an antibacterial amount of the compound of claim 4 and a conventional beta-lactam antibiotic in a weight ratio of 1:3 to 3:1.

8. A method of treating a bacterial infection in a mammal which comprises administering to said mammal an antibacterially effective amount of a pharmaceutical composition of claim 5.

9. A method of treating a bacterial infection in a mammal which comprises administering to said mammal an antibacterially effective amount of a pharmaceutical composition of claim 6.

10. A method of treating a bacterial infection in a mammal which comprises administering to said mammal an antibacterially effective amount of a pharmaceutical composition of claim 7.

11. A compound of the formula $$\underset{Y'O_2CCH=\overset{CH_3}{\underset{|}{C}}-NHCH_2\cdots}{}\underset{O}{\overset{H}{\underset{\|}{\phantom{X}}}}\underset{N}{\overset{O_2}{\underset{S}{\phantom{X}}}}\underset{\cdots COOR^1}{\overset{CH_3}{\underset{CH_3}{\phantom{X}}}} \quad (III)$$

or $$\underset{Y'O_2CCH=\overset{CH_3}{\underset{|}{C}}-NHCH_2}{}\underset{O}{\overset{H}{\underset{\|}{\phantom{X}}}}\underset{N}{\overset{O_2}{\underset{S}{\phantom{X}}}}\underset{\cdots COOR^1}{\overset{CH_3}{\underset{CH_3}{\phantom{X}}}} \quad (IV)$$

wherein Y' is $(C_1-C_3)$alkyl and $R^1$ is hydrogen, or a conventional ester forming radical which is hydrolyzable under physiological conditions, or cationic salts therof when $R^1$ is hydrogen.

12. A compound of claim 11 wherein said ester forming radical is:

[structures]

—$CHR^2OCOR^3$ or —$CHR^2OCOOR^3$,
wherein $R^2$ is hydrogen or methyl and $R^3$ is $(C_1-C_6)$alkyl.

13. A compound of claim 12 wherein $R^1$ is hydrogen,

[structures] or

14. A compound of claim 13 having the formula (III) wherein Y' is methyl.

15. The compound of claim 14 wherein $R^1$ is hydrogen in the form of its tetrabutylammonium salt.

16. The compound of claim 14 wherein $R^1$ is

[structure]

17. The compound of claim 14 wherein $R^1$ is

[structure]

* * * * *